United States Patent [19]

Lee

[11] 4,314,565
[45] Feb. 9, 1982

[54] BIOPSY AND ASPIRATION NEEDLE UNIT

[76] Inventor: Peter F. Lee, 6425 Vernon Ave., Edina, Minn. 55436

[21] Appl. No.: 88,818

[22] Filed: Oct. 26, 1979

Related U.S. Application Data

[63] Continuation-in-part of Ser. No. 883,263, Mar. 3, 1978, abandoned, which is a continuation of Ser. No. 706,130, Jul. 16, 1976, abandoned.

[51] Int. Cl.³ .............................................. A61B 10/00
[52] U.S. Cl. ..................................... 128/753; 128/754
[58] Field of Search ............... 128/753, 754, 752, 751, 128/310, 347, 348, 221; 279/20, 42; 408/226; 285/322, 323, 27, 330; 403/13, 14, 361, 341, 342

[56] References Cited

U.S. PATENT DOCUMENTS

| | | | |
|---|---|---|---|
| 449,246 | 3/1891 | Graham | 279/42 |
| 1,045,886 | 12/1912 | Reay | 279/42 |
| 1,585,934 | 5/1926 | Muir | 128/754 |
| 2,198,319 | 4/1940 | Silverman | 128/754 |
| 2,496,111 | 1/1950 | Turkel | 128/754 |
| 2,516,492 | 7/1950 | Turkel | 128/754 |
| 2,726,535 | 12/1955 | Turkel | 128/754 |
| 3,186,408 | 6/1965 | Jacob | 128/221 |
| 3,477,423 | 11/1969 | Griffith | 128/754 |
| 3,598,108 | 8/1971 | Jamshidi | 128/754 |
| 3,628,524 | 12/1971 | Jamshidi | 128/754 |

FOREIGN PATENT DOCUMENTS 379267 6/1973 U.S.S.R. ............................. 128/754

OTHER PUBLICATIONS

Miller et al, "Bone and Marrow Biopsy with Saw-Toothed Modification of Vim–Silverman Needle" 12-14-68.
Fajardo et al., "Technique for Percutaneous Needle Biopsy of Bone and Marrow" Aug.1972.
Pages 29-45, Being a subchapter entitled "Methods for the Study of the Bone Marrow" unknown textbook.
Conrad et al., "Bone Marrow Biopsy: Modification of the Vim–Silverman Needle" Apr. 1961.
Ackermann, "Application of the Trephine for Bone Biopsy" Apr. 1963.
Ellis et al., "Needle Biopsy of Bone and Marrow" Aug. 1964.
Stavem, "A New Bone Marrow Biopsy Needle" 1967.
Reddy, "A New Needle for Obtaining Undiluted Bone Marrow" Apr. 1952.
Rubinstein et al., "Superiority of Iliac Over Sternal Marrow Aspiration in Recovery of Neoplastic Cells".
Ackermann, "Vertebral Trephine Biopsy" Mar. 1956.
McFarland et al., "Biopsy of Bone Marrow with the Vim–Silverman Needle" Mar. 1958.
Dameshek, W., "Biopsy of the Sternal Bone Marrow, Its Value in the Study of Diseases" Nov. 1935.
Silverman, I., "A New Biopsy Needle" *Amer. Jour. of Surg.* Jun. 1938.
Turkel et al., "Biopsy of Bone Marrow Performed by a New and Simple Instrument" Sep. 1942.
Siffert et al., "Trephine Biopsy of Bone with Special Reference to the Lumbar Vertebral Bodies" Jan. 1949.

*Primary Examiner*—Michael H. Thaler
*Attorney, Agent, or Firm*—Merchant, Gould, Smith, Edell, Welter & Schmidt

[57] ABSTRACT

A bone marrow biopsy and aspiration needle unit is disclosed. The unit includes a holding device, with a longitudinal bore therethrough, comprising a collect chuck and handle grips, a replaceable cannula to be interlockably mounted in the holding means, with the cannula's lumen in alignment with the longitudinal bore, and an elongated stylet releaseably mounted in the aligned bores. When the needle unit is also to be used for aspiration, a second cannula of a diameter less than the first cannula is inserted through the aligned bores in the holding device and the first cannula.

5 Claims, 9 Drawing Figures

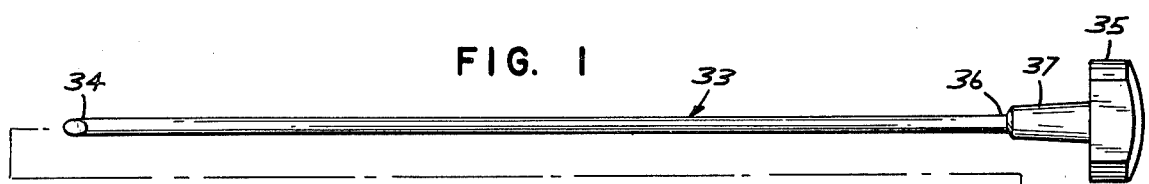
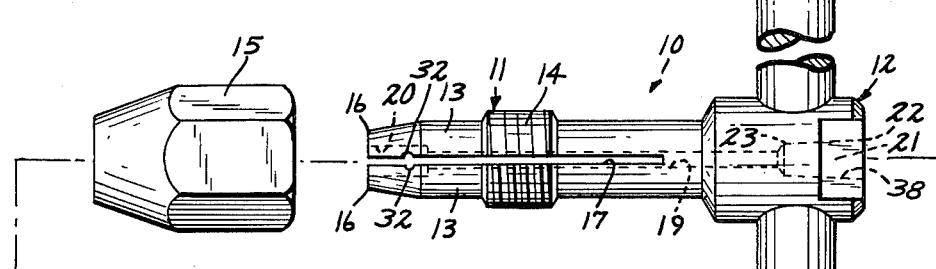
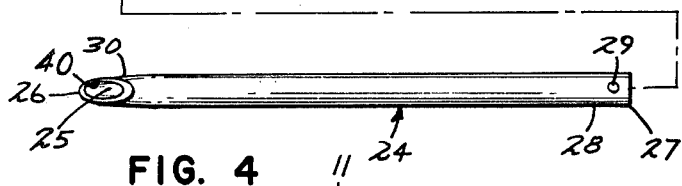
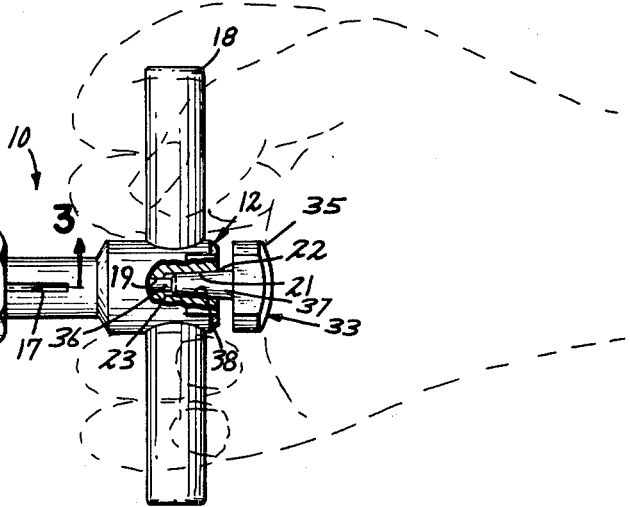
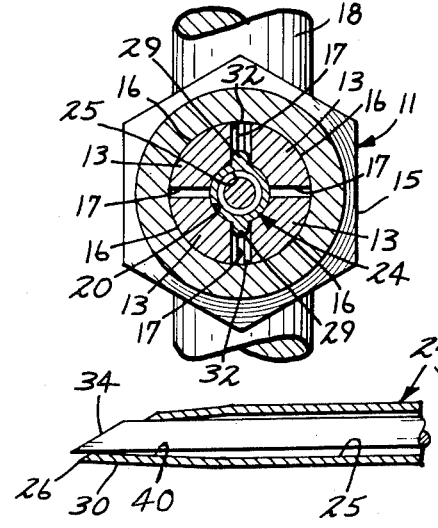
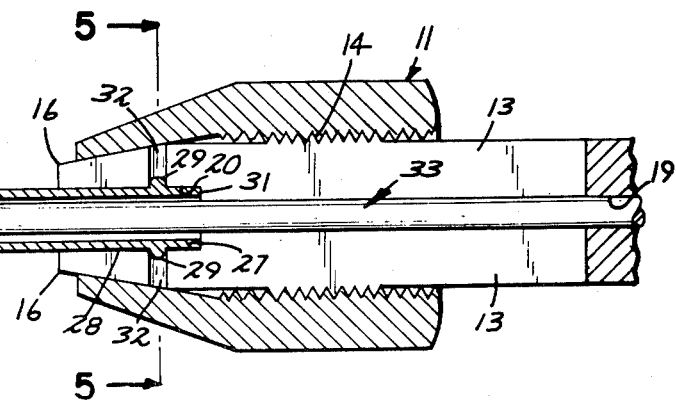

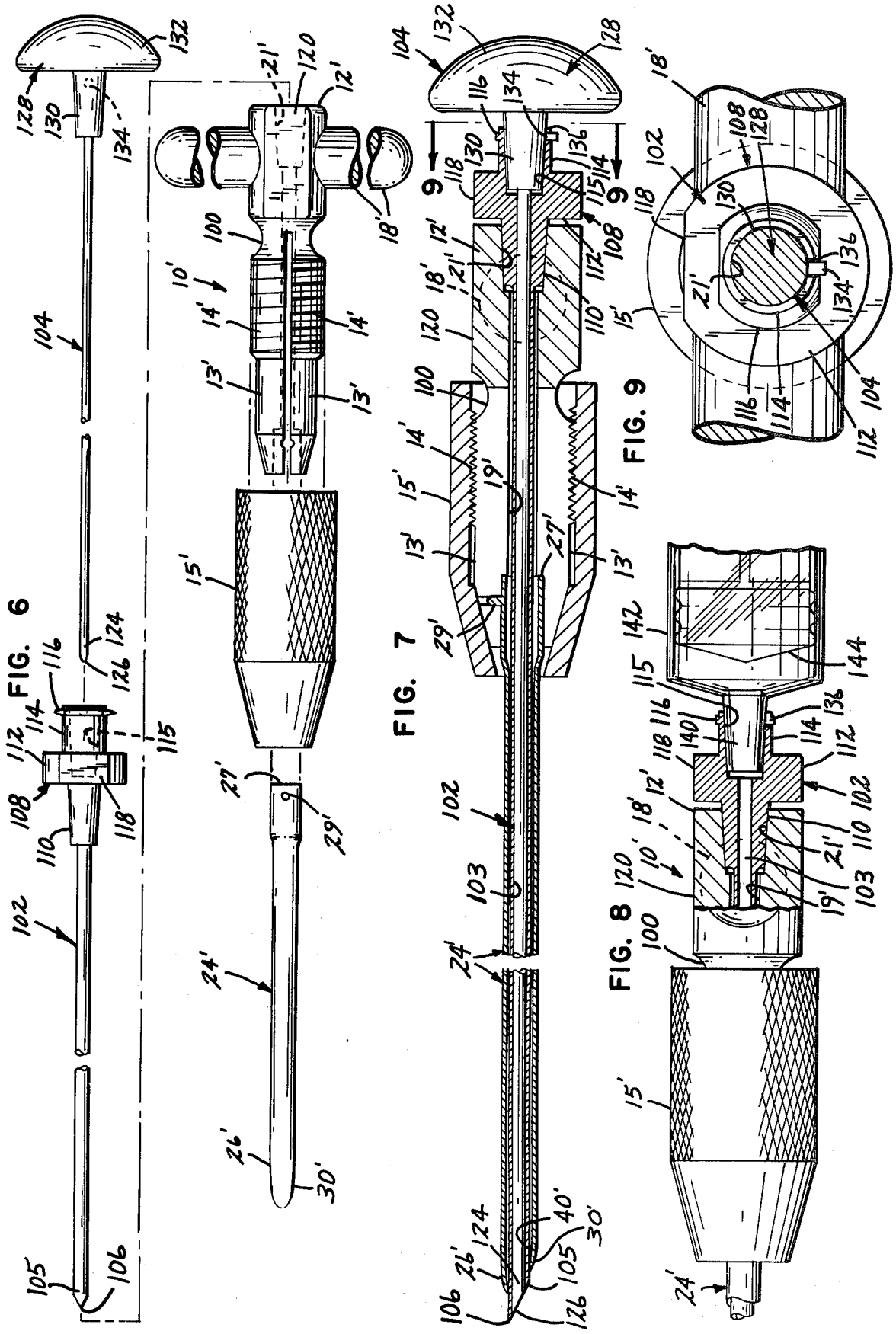

BIOPSY AND ASPIRATION NEEDLE UNIT

This application is a continuation-in-part of application filed Mar. 3, 1978, under Ser. No. 883,263, now abandoned, which is a continuation of Ser. No. 706,130 filed July 16, 1976, now abandoned.

TECHNICAL FIELD

This invention relates to the field of surgical tools and instruments. More particularly, it relates to the field of devices used to collect bone marrow tissue and fluid specimens for biopsy purposes.

BACKGROUND OF THE INVENTION

The advantages of examination of a bone marrow specimen undiluted with blood are well-known. Such an examination is essential for the evaluation of many hematologic disorders. A variety of devices have been used for collecting bone marrow specimens. Early bone marrow biopsies were taken from the sternum in operation-room procedures with scoop-like devices. Nonincisional methods utilizing the posterior iliac crest have proven less costly and less dangerous to the patient, and therefore more satisfactory. Such methods involve the introduction of a needle-like collecting device through the skin tissue, and the penetration of the bone cortex with the collecting device to take a small specimen of bone marrow tissue. Because of the pressure needed to bore through the cortex of the bone, and the subsequent cutting through of the trabeculae of the bone marrow, the cutting/collecting needles of prior devices have included integral finger grips of sturdy construction, such as those disclosed in Jamshidi, U.S. Pat. No. 3,628,524. The presence of such sturdy integral grips on the prior art collecting devices has made such devices expensive to use and maintain: the relatively high initial cost of the devices precludes one-time use, and multiple-time use requires resterilization of the device prior to each use and resharpening of the cutting edges. Needle lumens are difficult to clean. Tissue or proteinaceous matter left in the lumen can result in pyrogens that are unaffected by heat sterilization. Resharpening requires time and special skills. Thus, the amount of handling required by the prior art devices leads to high costs and increased chance for human error.

It is often desirable to aspirate fluids from bone tissue in addition to taking bone marrow tissue itself. Numerous devices have been available to aspirate fluids from bone tissue. Such prior art aspiration devices, however, have either been separate from the prior art devices used to take bone marrow tissue samples, or have used a bone marrow biopsy unit for aspiration. However, a bone marrow biopsy unit generally does not have the optimum diameter for aspirating fluids.

SUMMARY OF THE INVENTION

The object of this invention is to provide a biopsy device that will allow for the interchange of various lengths and gauges of presterilized, pyrogen-free, single-use needles capable of obtaining and retrieving a superior histologic, undistorted bone marrow specimen at an economical cost and with minimum patient discomfort. This object is accomplished in the present invention by utilizing a permanent needle-holding means and a replaceable cutting/collecting needle, or cannula, in conjunction with a stylet. The cannula is a hollow needle with an inner and outer taper at its distal end. The holding means incorporates a collet chuck and handle grips. The holding means has a bore along its longitudinal axis to accomodate the stylet. Since, in use, strong compression, tension, and twisting forces are applied along and around the longitudinal axis of the unit, the cannula must be securely mounted in the holding means to prevent any slippage of the cannula during its insertion and removal. This secure mounting is achieved by counterboring the jaw portion of the collet chuck to accomodate a replaceable cannula, which is of a generally larger diameter than the longitudinal bore in the holding means. The interface of the jaw counterbore with the longitudinal bore defines an annular end wall, against which the proximal end of the cannula abuts when mounted, thus preventing the cannula from slipping further into the holding means while being inserted through the bore cortex. The jaw counterbore is also provided with at least one recessed portion, which coincides with at least one raised portion on the external proximal end surface portion of the cannula, so that when the proximal end of the cannula is placed in the jaw counterbore and the jaws are tightened around the cannula by tightening the collar nut of the collet chuck, the raised portion of the cannula interlocks with the recessed portion of the jaw counterbore. This interlock prevents movement of the cannula around the longitudinal axis of the unit when a twisting force is applied thereto, and it also prevents the cannula from slipping out of the holding means when a pulling force is exerted on the holding means to remove the cannula from the bone cavity. Thus, the structural advantages of the one-piece, prior art cannula/handle units are preserved, while at the same time the advantages of an inexpensive, replaceable cannula are gained.

The invention is further directed to a needle unit capable of both retrieving a bone marrow specimen and aspirating fluids. In order to accomplish this dual function, the needle unit includes a second cannula which has an outer diameter less than the inner diameter of the cannula and the bore through the holding means. In this manner, the second cannula is inserted through the top of the holding means and passes through the longitudinal bore therein and through the hollow interior of the first cannula. The second cannula has a hollow interior extending throughout its entire length of an inner diameter appropriate for aspirating fluids. The outer end of the second cannula friction fits within a counterbore in the top of the holding means. A second stylet is inserted through the hollow interior of the second cannula during the insertion of the needle unit into a bone. In order to aspirate a fluid sample, the stylet is removed and an empty syringe is friction fit into the top of the second cannula. By withdrawing the plunger of the syringe, a fluid sample is aspirated. After the aspiration procedure has been accomplished, the second cannula can be removed and the first stylet replaced therefor. The needle unit can thereafter be moved further into the bone and the first stylet removed at the appropriate point to collect a bone marrow tissue specimen.

BRIEF DESCRIPTION OF THE DRAWINGS

FIG. 1 is an exploded elevation of the biopsy needle unit;

FIG. 2 is a view in elevation of the assembled biopsy needle unit;

FIG. 3 is a sectional view of a portion of the biopsy needle unit as seen from the line 3—3 of FIG. 2;

FIG. 4 is a fragmentary plane view of a portion of FIG. 2 with parts removed therefrom;

FIG. 5 is a sectional view as seen from the line 5—5 of FIG. 3;

FIG. 6 is an exploded elevation of the needle unit for use in aspirating fluids;

FIG. 7 is a longitudinal sectional view, partially broken away, of the assembled needle unit for aspirating fluids;

FIG. 8 is a partial view in elevation, partially broken away, illustrating a syringe inserted into the second cannula; and FIG. 9 is a view taken generally along line 9—9 of FIG. 7.

DESCRIPTION OF THE PREFERRED EMBODIMENT

FIG. 1 shows the elements of a bone marrow biopsy unit. Generally T-shaped holding means 10 include a collet chuck 11 and a head portion 12. Collet chuck 11 comprises a plurality of arms 13 with external threading 14 thereon to engage collar nut 15. Each arm 13 terminates in a jaw portion 16, and is separated from each other arm 13 by a compressible, generally planar space, or slot 17, running the length of each arm 13. A handle 18 extends from head portion 12 at generally right angles to the longitudinal axis of holding means 10. A longitudinal bore 19 of circular cross section runs along the longitudinal axis and through head portion 12 and collect chuck 11. A first counterbore 20 of uniform circular cross section runs along the longitudinal axis through jaw portions 16, and a second counterbore 21 runs along the longitudinal axis in head portion 12. Second counterbore 21 tapers uniformly from a first diameter 22 to a smaller, second diameter 23, which is larger than the diameter of longitudinal bore 19.

A replaceable cannula 24 has a bore, or lumen 25, an open distal end 26, which defines a cutting edge outwardly beveled and obliquely disposed to the longitudinal axis of cannula 24, an open proximal end 27, and an external proximal end surface portion 28 with raised portions. In this embodiment two hemispherical beads 29 are annularly disposed 180° apart thereon, as indicated in FIGS. 3 and 5. Cannula 24 has a generally circular cross section of uniform inside and outside diameter along the major portion of its length and internal and external distal end portions 40 and 30 uniformly tapered toward distal end 26.

First counterbore 20 is of a diameter generally equal to the outside diameter of cannula 24 at proximal end 27. Said diameter is larger than the diameter of longitudinal bore 19. An annular end wall 31 is formed at the interface of longitudinal bore 19 and first counterbore 20.

Jaw portions 16 have recesses, grooves 32 in the preferred embodiment, to interlock with beads 29 when cannula 24 is mounted in holding means 10. Grooves 32 are generally in the planes defined by slots 17 and are along an axis transverse to the longitudinal axis of the holding means 10, as depicted in FIGS. 3 and 5. Each groove 32 has a semicircular cross section of radius corresponding to the radii of beads 29.

Beads 29, grooves 32, and end wall 31 comprise a means for interlockingly mounting cannula 24 in holding means 10, which is accomplished by placing proximal end 27 in first counterbore 20, as shown in FIG. 4, and tightening collar nut 15 as shown in FIG. 3. When so mounted, lumen 25 is aligned with longitudinal bore 19.

An elongated stylet 33 has distal end 34 defining a sharpened cutting edge obliquely disposed to the longitudinal axis of stylet 33 at an angle equal to that at which distal end 26 is disposed to the longitudinal axis of cannula 24, as shown in FIG. 3. Stylet 33 has a cap portion 35 at its proximal end 36 having an elongated stem portion 37. Stem portion 37 has a tapered circular cross section corresponding to that of second counterbore 21. When stylet 33 is releaseably mounted in the aligned longitudinal bore 19 of holding means 10 and lumen 25 of the mounted cannula 24, as shown in FIG. 3 stem portion 37 frictionally engages the interior surface 38 of second counterbore 21 as shown in FIG. 2, and distal end 34 extends a predetermined distance beyond distal end 26 to prevent bone matter from entering lumen 25 while the unit is boring through the bone cortex to the bone cavity. In the preferred embodiment, the predetermined distance is two millimeters.

In use, replaceable cannula 24 is interlockingly mounted in holding means 10, and stylet 33 is releaseably mounted in the aligned longitudinal bore 19 and lumen 25 with stem portion 37 frictionally engaging interior surface 38 of second counterbore 21. Cannula 24, with stylet 33 in place, is then inserted through the skin tissue of a patient to the bone cortex.

Longitudinal and twisting forces are applied to holding means 10 until distal ends 26 and 34 enter the bone cavity, at which time stylet 33 is removed from aligned bore 19 and lumen 25. Cannula 24 is then forced several centimeters further into the bone cavity to collect a specimen of marrow tissue in lumen 25, after which cannula 24 is removed from the bone cavity and patient by exerting a pulling force on holding means 10. The specimen is removed from lumen 25 by first removing cannula 24 from holding means 10, and then inserting stylet 33 into lumen 25 by way of distal end 26 and gently probing the specimen to force it out of lumen 25 at proximal end 27.

Cannula 24, being a relatively inexpensive element of the unit, can be disposed or before resterilization and resharpening are required, and replaced by a new, presterilized cannula of the requisite length and gauge for use in subsequent specimen-gathering instances, thus accomplishing the objectives of the invention.

FIGS. 6–9 illustrate an embodiment of the present invention which can be used to aspirate fluid from bone tissue, in addition to extracting bone marrow tissue. Portions of the needle unit illustrated in the FIGS. 6–9 which are similar portions of the unit illustrated in FIGS. 1–5, will be designated by like primed numerals.

The holding means 10' and the replaceable cannula 24' are the same as the holding means 10 and the cannula 24, except in the following minor details. The taper of the distal end 26' of the cannula 24' is reduced. The open proximal end 27' is flared outwardly to a greater diameter than the remaining portion of the cannula 24'; and only a singular bead 29' is utilized. The collar nut 15' is slightly longer than the collar nut 15 and has a round knurled outer surface. The external threading 14' on the arms 13' extends over a slightly longer longitudinal length. The outer ends of the handle 18' are rounded. An annular cutout 100 is formed in the holding means 10' at a location between the threaded portion 14' of the arms 13' and the head portion 12'.

So that the needle unit can aspirate fluid in addition to exracting the bone marrow tissue, a second cannula 102 and a second stylet 104 are provided.

The second cannula has an outer diameter less than the inner diameter of the first cannula 24' and the longitudinal bore 19' of the holding means 10'. In this manner, the second cannula 102 can be received within the first cannula 24' and the holding means 10'. The second cannula 102 has a bore or lumen 103 with an inner diameter which is necessarily less than the inner diameter of the first cannula 24' and is of the proper size for the aspiration of fluids from bone tissue. The second cannula 102 has an open distal end 105 with a sharpened cutting edge 106 obliquely disposed to the longitudinal axis of the cannula 102. The second cannula 102 also has a proximal end or head portion 108. The proximal end 108 includes a tapered engagement section 110, an alignment ring 112, and a cylindrical section 114 with a coupling collar 116. The engagement section 110 has a taper which mates with the taper of the counterbore 21' so that the engagement section 110 can frictionally engage with the counterbore 21' of the holding means 10'. The alignment collar 112 has a flat 118 and the head portion 12' has a flat 120. By aligning the flat 118 with the flat 120, the angle at which the cutting edge 106 is disposed can be aligned with the angle at which the proximal end 26' is cut. See FIG. 8. The head portion 108 also has a counterbore 115 through it in alignment with the lumen 103. The counterbore 115 has an inner diameter which tapers radially outwardly from a small diameter, which is larger than the diameter of the lumen 103, to a larger diameter.

The stylet 104 has a distal end 124 with a sharpened cutting edge 126 obliquely disposed to the longitudinal axis of the cannula 102. The stylet 104 has a proximal end 128 with a tapered engagement or stem portion 130 and a cap portion 132. The stem portion 130 has a tapered circular cross section corresponding to that of the counterbore 115 of the proximal end 108 of the second cannula 102. A finger or pin 134 extends outwardly from the stem portion 130 and is received within a slot 136 formed through the cylindrical section 114 and the coupling collar 116. In this manner, the stylet 104 is frictionally held by the mating engagement between the outer surface of the stem portion 130 and the inner surface of the counterbore 115, and the angle at which the cutting edge 126 is set is aligned with the angle of the cutting edge 106 by inserting the finger 134 within the slot 136.

The needle unit is used in the following manner to obtain a fluid sample. The cannula 24', the cannula 102 and the stylet 104 are assembled and inserted into a bone cavity to a point where a fluid sample is to be taken. Thereafter the stylet 104 is removed and a tip 140 of a syringe 142 is inserted into the counterbore 115. A plunger 144 of the syringe 142 is pulled back within a cylinder of the syringe 142 in order to aspirate fluid. The fluid is drawn through the cannula 102 into the cylinder of the syringe 142. The syringe is thereafter removed from the second cannula 102 and the fluid in the syringe can thereafter be removed from the syringe 142 for further testing or treatment. If a bone tissue sample is also required, the cannula 24' can be further inserted into the bone tissue in the same manner as the cannula 24.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent extended by the broad general meaning of the terms in which the appended claims are expressed.

What is claimed is:

1. A bone marrow biopsy needle unit comprising:
    (a) holding means including a collet chuck and a head portion aligned coaxially so that a line running along the common axis defines a longitudinal axis of said holding means, a bore of circular cross section along said longitudinal axis through said head portion and said collet chuck, and handle means extending from said head portion generally at right angles to said longitudinal axis, said collet chuck comprising a plurality of arms with external threading thereon, adjacent arms being separated by said generally longitudinally extending slot, each arm terminating in a jaw portion, and a collar nut to threadedly engage and radially compress said arms, each arm having an interior surface, said interior surfaces defining a segmented cylinder generally of a first diameter when said arms are not compressed by said collar nut;
    (b) a replaceable cannula, of predetermined length and gauge, of uniform hollow cylindrical configuration throughout the major portion of its length, having an open distal end, an external distal end surface portion uniformly tapered toward said distal end and an internal distal end surface portion tapered uniformly from a first circular diameter which extends along the major portion of said length of said cannula to a smaller circular diameter at said distal end, said distal end defining a cutting edge which is outwardly beveled and is obliquely disposed to the longitudinal axis of said cannula, an open proximal end, and an external proximal end surface portion, said proximal end having a second diameter generally equal to said first diameter and being adapted to be releasably mounted in said collet chuck with a bore thereof being coaxially aligned with said bore of said holding means;
    (c) interlocking means for preventing movement of said cannula along or around said longitudinal axis of said holding means when said proximal end of said cannula is mounted in said collet chuck, said interlocking means comprising a protrusion and a recess, said protrusion extending from said proximal end portion of said cannula in a direction generally radial from said longitudinal axis a distance beyond said first diameter into one of said slots, said protrusion having an abutment surface facing in a direction of rotation about said longitudinal axis, said recess extending into at least one of said arms from an edge of said last-mentioned arm defining one of said slots into said last-mentioned arm in a direction of rotation about said longitudinal axis to define an abutment edge facing in a direction of rotation about said longitudinal axis, said abutment surface and abutment edge mating when said cannula is connected to said chuck to prevent the rotation of said cannula with respect to said chuck;
    (d) an elongated stylet, of predetermined length and gauge, of generally uniform circular cross section mounted in said aligned bores, said stylet having a distal end, a proximal end, and a cap portion at said proximal end; and (e) engaging means on both said stylet and said head portion cooperating to releasably engage said stylet and said holding means.

2. The biopsy needle unit of claim 1 wherein said interlocking means include an annular end wall in said collet chuck formed at the interface of said bore of said holding means and a larger diameter counterbore along said longitudinal axis through said jaw portions, said counterbore being defined at least in part by the inner surface of said arms and being of said second diameter generally equal to the outside first diameter of said cannula at said proximal end, said protrusion being formed as a hemispherical bead external from said external proximal end surface portion of said cannula, and a pair of said recesses, one of said recesses being formed in said one opposed edge of one of the arms defining one of the slots, said recesses being opposite one another and of a size and shape corresponding to that of said bead, so that when said proximal end of said replaceable cannula is abutting said annular wall and said collar nut is tightened, said beads interlock with said opposite recesses.

3. The biopsy needle unit of claim 1 wherein said cap portion of said stylet comprises a knob portion and an elongated stem portion, said stem portion having a generally circular cross section uniformly tapering from one diameter to a second, smaller diameter at said proximal end of said stylet; said engaging means comprising said elongated stem portion and an interior surface formed by a counterbore along said longitudinal axis of said holding means in said head portion, said counterbore being uniformly tapered to correspond with the taper of said stem portion, so that when said stylet is mounted in said aligned bores, said interior surface formed in said head portion frictionally engages said stem portion.

4. The biopsy needle unit of claim 1 wherein said stylet is of a length such that, when mounted in said aligned bores, said distal end of said stylet extends a predetermined distance of approximately two millimeters beyond said distal end of said cannula.

5. A bone marrow biopsy needle unit comprising:
(a) generally T-shaped holding means including:
  (i) a collet chuck and a head portion aligned coaxially, the common axis defining the longitudinal axis of said holding means, said collet chuck comprising a plurality of arms with external threading thereon to engage a collar nut, said collar nut radially compressing said arms when threaded thereon, each said arm terminating in a jaw portion, and each said arm being separated from each other said arm by a compressible, generally planar, slot running the length of each said arm, each arm having a longitudinally extending edge defining a longitudinal end of said slot;
  (ii) a handle extending from said head portion at generally right angles to said longitudinal axis,
  (iii) a longitudinal bore of circular cross section along said longitudinal axis through said head portion and said collet chuck, a first counter-bore of uniform circular cross section of larger diameter than that of said longitudinal bore along said longitudinal axis through said jaw portions, and a second counterbore along said longitudinal axis in head portion uniformly tapering from a first diameter to a smaller second diameter, said second diameter being greater than the diameter of said longitudinal bore;

(b) a replaceable cannula having a lumen; an open distal end, an open proximal end, and an external proximal end surface portion with a hemispherical bead disposed thereon and extending therefrom adapted to be releasably mounted in said holding means so that said lumen is coaxially aligned with said longitudinal bore, said bead having an abutment surface facing in a direction of rotation about said longitudinal axis, said cannula having a generally circular cross section of uniform inside and outside diameter along the major portion of its length and internal and external distal end portions uniformly tapered toward said distal end, said distal end defining a cutting edge which is outwardly beveled and is obliquely disposed to the longitudinal axis of said cannula;

(c) a recess formed in each longitudinally extending edge defining one of said slots, each recess having an abutment edge facing a direction of rotation about said longitudinal axis, and each said recess having a semicircular cross section of radius corresponding to the radii of said hemispherical bead; and (d) an elongated stylet of generally uniform circular cross section releasably mounted in said aligned longitudinal bore and lumen, said stylet having a distal end defining a cutting edge obliquely disposed to that longitudinal axis of said stylet at an angle equal to that at which said distal end of said cannula is disposed to said longitudinal axis of said cannula, a proximal end, and a cap portion at said proximal end having an elongated stem portion of tapered circular cross section corresponding to the taper of said second counterbore to frictionally engage said head portion, said stylet being of such a length that when mounted, said distal end of said stylet extends a predetermined distance beyond said distal end of said mounted cannula.

* * * * *